United States Patent
Madin et al.

(10) Patent No.: US 7,144,910 B2
(45) Date of Patent: Dec. 5, 2006

(54) SULFONAMIDES, SULFAMATES AND SULFAMIDES AS GAMMA-SECRETASE INHIBITORS

(75) Inventors: Andrew Madin, Sawbridgeworth (GB); Mark Peter Ridgill, Watton-at-Stone (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 91 days.

(21) Appl. No.: 10/533,151

(22) PCT Filed: Oct. 29, 2003

(86) PCT No.: PCT/GB03/04707

§ 371 (c)(1),
(2), (4) Date: Apr. 27, 2005

(87) PCT Pub. No.: WO2004/039370

PCT Pub. Date: May 13, 2004

(65) Prior Publication Data

US 2006/0069147 A1    Mar. 30, 2006

(30) Foreign Application Priority Data

Nov. 1, 2002 (GB) ................. 0225474.6

(51) Int. Cl.
*A61K 31/415* (2006.01)
*C07D 231/10* (2006.01)
(52) U.S. Cl. .................. 514/406; 548/364.1; 548/377.1
(58) Field of Classification Search ............... 514/406; 548/364.1, 377.1
See application file for complete search history.

(56) References Cited

FOREIGN PATENT DOCUMENTS

| WO | WO 01/70677 | 9/2001 |
|---|---|---|
| WO | WO 02/36555 | 5/2002 |

*Primary Examiner*—Kamal A. Saeed
(74) *Attorney, Agent, or Firm*—John C. Todaro; Melvin Winokur

(57) ABSTRACT

Compounds of formula I:

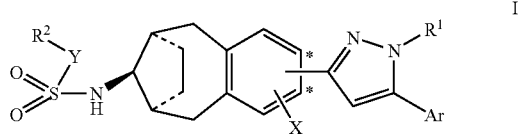

inhibit the processing of APP by gamma-secretase, and hence are useful in treating or preventing Alzheimer's disease.

10 Claims, No Drawings

SULFONAMIDES, SULFAMATES AND SULFAMIDES AS GAMMA-SECRETASE INHIBITORS

CROSS REFERENCE TO RELATED APPLICATIONS

This application is a U.S. National Phase application under 35 U.S.C. § 371 of PCT Application No. PCT/GB03/004707, filed Oct. 29, 2003, which claims priority under 35 U.S.C. § 119 from GB Application No. 0225474.6, filed Nov. 1, 2002.

The present invention relates to a novel class of compounds, their salts, pharmaceutical compositions comprising them, processes for making them and their use in therapy of the human body. In particular, the invention relates to novel sulfonamide, sulfamate and sulfamide derivatives which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are relatively few reports in the literature of compounds with inhibitory activity towards γ-secretase, as measured in cell-based assays. These are reviewed in WO 01/0677. Many of the relevant compounds are peptides or peptide derivatives.

WO 01/70677 and WO 02/36555 disclose, respectively, sulfonamido- and sulfamido-substituted bridged bicycloalkyl derivatives which are believed to be useful in the treatment of Alzheimer's disease, but do not disclose or suggest compounds in accordance with the present invention.

The present invention provides a novel class of bridged bicycloalkyl sulfonamide, sulfamate and sulfamide derivatives which show a particularly strong inhibition of the processing of APP by the putative γ-secretase, and thus are useful in the treatment or prevention of AD.

According to the invention there is provided a compound of formula I:

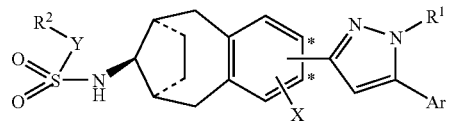

wherein the pyrazole group is attached at one of the positions indicated by an asterisk and X is attached at a position adjacent thereto;

X represents H, OH, $C_{1-4}$alkoxy, Cl or F;

Y represents a bond, O or $NR^3$;

Ar represents phenyl or 6-membered heteroaryl, either of which bears 0–3 substituents independently selected from halogen, $CF_3$, $CHF_2$, $CH_2F$, $NO_2$, CN, $OCF_3$, $C_{1-6}$alkyl and $C_{1-6}$alkoxy;

$R^1$ represents a hydrocarbon group of 1–5 carbon atoms which is optionally substituted with up to 3 halogen atoms; and $R^2$ represents a hydrocarbon group of 1–10 carbon atoms which is optionally substituted with up to 3 halogen atoms, or heteroaryl of 5 or 6 ring atoms optionally bearing up to 3 substituents independently selected from halogen, $CF_3$, $CHF_2$, $CH_2F$, $NO_2$, CN, $OCF_3$, $C_{1-6}$allyl and $C_{1-6}$alkoxy; or when Y represents $NR_3$, $R^2$ and $R^3$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy, $R^3$ represents H or $C_{1-4}$alkyl, or together with $R^2$ completes a heterocyclic ring as defined above;

or a pharmaceutically acceptable salt thereof.

It will be readily apparent to those skilled in the art that any compound in accordance with formula I may exist in two enantiomeric forms, depending on which of the ring positions indicated by an asterisk is bonded to the pyrazole ring. Formula I thus encompasses enantiomers of formulae IIa and IIb:

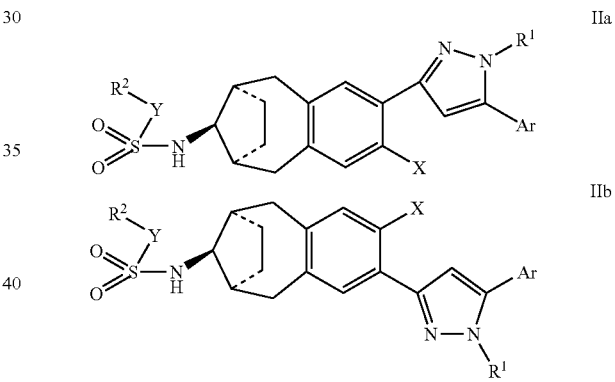

wherein X, Y, Ar, $R^1$ and $R^2$ are as defined previously;

and also enantiomers of formulae IIIa and IIIb:

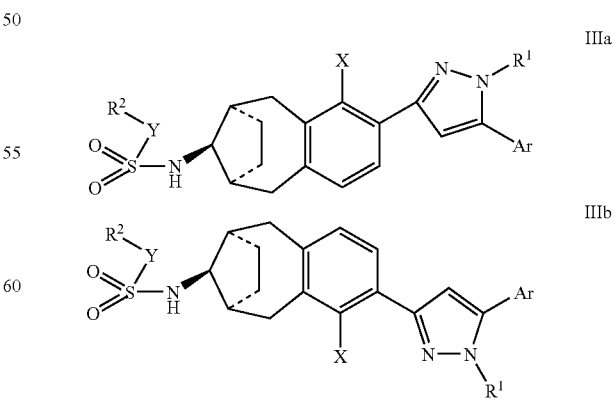

wherein X, Y, Ar, $R^1$ and $R^2$ are as defined previously.

It will also be apparent that when X represents H formula IIa is identical to formula IIIa and formula IIb is identical to formula IIIb.

It is to be emphasised that the invention, for each compound in accordance with formula I, encompasses both enantiomeric forms, either as homochiral compounds or as mixtures of enantiomers in any proportion.

In a preferred embodiment of the invention, the compound of formula I is a homochiral compound of formula IIa or formula IIIa, or a pharmaceutically acceptable salt thereof.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$ayrl" and "$C_{1-6}$alkoxy" are to be construed in an analogous manner. Most suitably, the number of carbon atoms in such groups is not more than 6.

The expression "$C_{3-6}$cycloallyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

The expression "cycloalkylalkyl" as used herein includes groups such as cyclopropylmethyl, cyclobutylmethyl, cyclopentylmethyl and cyclohexylmethyl.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, benzenesulfonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, X preferably represents H, OH or F, more preferably H or F. In one particular embodiment, X is H. In another particular embodiment, X is F. Most preferably, X is H.

Ar represents phenyl or 6-membered heteroaryl, either of which bears 0–3 substituents independently selected from halogen, $CF_3$, $CHF_2$, $CH_2F$, $NO_2$, CN, $OCF_3$, $C_{1-6}$alkyl and $C_{1-6}$alkoxy. Examples of suitable 6-membered heteroaryl groups represented by Ar include pyridyl, pyrazinyl, pyrimidinyl, pyridazinyl and triazinyl, of which pyridyl is a preferred example. Preferably, the phenyl or heteroaryl ring bears 0 to 2 substituents. Preferred substituents include halogen (especially chlorine and fluorine), CN, $C_{1-6}$alkyl (especially methyl), $C_{1-6}$alkoxy (especially methoxy), $OCF_3$ and $CF_3$. If two or more substituents are present, preferably not more than one of them is other than halogen or alkyl. Examples of groups represented by Ar include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for Ar include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 4-cyanophenyl, 4-methylphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2yl, 5-chloropyridin-2-yl, 5-(trifluoromethyl)pyridin-2-yl and 6-(trifluoromethyl)pyridin-3-yl. Preferred examples include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 4-(trifluoromethyl)phenyl, pyridin-2-yl, pyridin-3-yl and pyridin-4-yl.

In a particularly preferred embodiment, Ar represents 4-fluorophenyl.

$R^1$ represents a hydrocarbon group of 1–5 carbon atoms which is optionally substituted with up to 3 halogen atoms, and thus may comprise cyclic or acyclic hydrocarbon residues or combinations thereof, saturated or unsaturated, up to a maximum of 5 carbon atoms in total. The hydrocarbon group represented by $R^1$ is preferably unsubstituted or is substituted with up to 3 fluorine atoms Examples include methyl, ethyl, n-propyl, isopropyl, n-butyl, sec-butyl, t-butyl, fluoromethyl, difluoromethyl, trifluoromethyl, 2,2,2-trifluoroethyl, cyclopropyl, cyclopropylmethyl and allyl. Preferred examples include methyl, ethyl and 2,2,2-trifluoroethyl. Most preferably, $R^1$ represents methyl.

Suitable hydrocarbon groups represented by $R^2$ include alkyl, cycloalkyl, cycloalkylalkyl, alkenyl, phenyl and benzyl groups optionally bearing up to 3 halogen substituents, the preferred halogen substituent being fluorine or chlorine, especially fluorine. Said alkyl, cycloalkyl, cycloalkylalkyl and alkenyl groups typically comprise up to 6 carbon atoms. Examples of hydrocarbon and fluorinated hydrocarbon groups represented by $R^2$ include 4-fluorophenyl, benzyl, n-propyl, 2,2-dimethylpropyl, n-butyl, isopropyl, t-butyl, 2,2,2-trifluoroethyl, 3,3,3-trifluoropropyl, allyl, cyclopropyl, cyclobutyl and cyclopropylmethyl.

Heteroaryl groups represented by $R^1$ are either 5-membered or 6-membered and are optionally substituted as defined previously. Preferred 5-membered heteroaryl groups include those containing a sulfur atom, such as thienyl, thiazolyl and isothiazolyl. Preferred 6-membered heteroaryl groups include pyridyl, in particular 3-pyridyl. Preferred substituents include halogen (especially chlorine or fluorine), $CF_3$ and alkyl (such as methyl). If two or more substituents are present, preferably not more than one of them is other than halogen or alkyl. Preferred heteroaryl groups are unsubstituted or monosubstituted with halogen.

When $R^2$ represents an optionally substituted phenyl or heteroaryl group, Y is preferably a bond.

When Y represents $NR^3$, $R^2$ may combine with $R^3$ to complete a heterocyclic ring of up to 6 members which is optionally substituted as defined previously. Said ring preferably comprises at most one heteroatom selected from O, N and S in addition to the nitrogen to which $R^2$ and $R^3$ are mutually attached. Suitable rings include azetidinyl, pyrrolidinyl, piperidinyl, piperazinyl, morpholinyl and thiomorpholinyl. Preferred substituents include $CF_3$, halogen (especially chlorine or fluorine) and alkyl such as methyl. If two or more substituents are present, preferably not more than one of them is other than halogen or alkyl.

$R^3$ may alternatively represent H or $C_{1-4}$alkyl, such as methyl Preferably, $R^3$ represents H or completes a ring with $R^2$.

In one subset of the compounds of formula I, Y is a bond and $R^2$ is hydrocarbon of up to 6 carbon atoms, optionally bearing up to 3 fluorine or chlorine substituents, or 5- or 6-membered heteroaryl which is optionally substituted as described previously. Within this embodiment, suitable identities for $R^2$ include n-butyl, 4-fluorophenyl, 2-thienyl, 5-chloro-2-thienyl, 5-isothiazolyl and 6-chloro-3-pyridyl.

In a second subset of the compounds of formula I, Y is O and $R^2$ represents alkyl, alkenyl, cycloalkyl or cycloalkylalkyl of up to 6 carbon atoms which is optionally substituted with up to 3 fluorine atoms.

In a third subset of the compounds of formula I, Y is NH or NMe and $R^2$ represents alkyl, alkenyl, cycloalkyl or cycloalkylalkyl of up to 6 carbon atoms which is optionally substituted with up to 3 fluorine atoms.

In a fourth subset of the compounds of formula I, Y represents $NR^3$ and $R^2$ and $R^3$ complete a heterocyclic ring as described previously.

Specific examples of compounds in accordance with the invention include the compounds of formula IIIa or formula IIa in which X is H, Ar is 4-fluorophenyl, $R^1$ is methyl and Y, $R^2$ and (where relevant) $R^3$ are as shown in the following table:

| Y | $R^2$ | $R^3$ |
|---|---|---|
| bond | n-butyl | — |
| bond | 4-fluorophenyl | — |
| bond | 5-chloro-2-thienyl | — |
| bond | 5-isothiazolyl | — |
| bond | 6-chloropyridin-3-yl | — |
| bond | 2-thienyl | — |
| O | n-propyl | — |
| O | cyclobutyl | — |
| $NR^3$ | 2,2,2-trifluoroethyl | H |
| $NR^3$ | n-propyl | H |
| $NR^3$ | n-propyl | methyl |
| $NR^3$ | cyclobutyl | H |
| $NR^3$ | methyl | methyl |
| $NR^3$ | pyrrolidinyl | |
| $NR^3$ | 4-(trifluoromethyl)piperidinyl | |
| $NR^3$ | cyclopropyl | H |

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of the invention or a pharmaceutically acceptable salt thereof for use in a method of treatment of the human body. Preferably the treatment is for a condition associated with the deposition of p-amyloid. Preferably the condition is a neurological disease having associated p-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's disease, a suitable dosage level is about 0.01 to 250 mg/kg per day, preferably about 0.01 to 100 mg/kg per day, more preferably about 0.05 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

The compounds of formula I may be prepared by reaction of an amine (1) with $R^2$—Y—$SO_2Cl$:

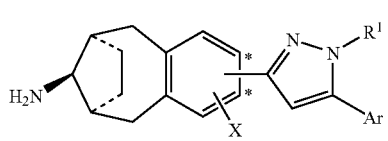
(1)

where X, Y, Ar, $R^1$ and $R^2$ have the same meanings as before. The reaction takes place in an aprotic solvent such as dichloromethane in the presence of a base such as triethylamine or pyridine.

The amines (1) may be prepared by treatment of the sulfinamides (2) with acid:

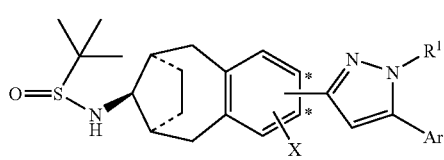
(2)

where X, Ar and $R^1$ have the same meanings as before. The reaction may be carried out at 0° C. using anhydrous HCl in dioxan.

The sulfinamides (2) are available from the reduction of imines (3a), which are in turn available from the condensation of ketones (3b) with t-Bu-SO—$NH_2$:

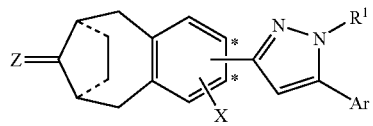
(3)

(a) Z = t-Bu—S(O)—N
(b) Z = O where X, Ar and $R^1$ have the same meanings as before. The condensation takes place in refluxing TBF in the presence of titanium (IV) ethoxide, while the reduction may be effected using sodium borohydride in methanol at 0° C.

The ketones (3b) may be prepared by coupling of boronates (4) with pyrazole derivatives (5):

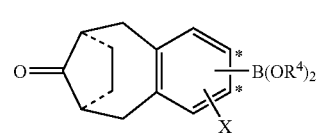
(4)

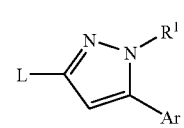
(5)

wherein $R^4$ represents H or $C_{1-6}$alkyl, or the two $OR^4$ groups complete a cyclic boronate ester such as the pinacolate, L represents a leaving group such as triflate, bromide or iodide (preferably triflate), and X, Ar and $R^1$ have the same meanings as before. The coupling takes place in the presence of a Pd catalyst such as tetrakis(triphenylphosphine)palladium (0), typically in the presence of an inorganic base such as potassium acetate or potassium carbonate in DMF at 100° C.

Boronates (4) may be prepared by reaction of triflates (6) with a suitable boron reagent, such as bis(pinacolato)diboron:

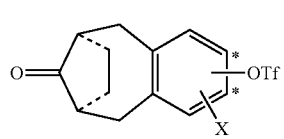
(6)

wherein Tf represents trifluoromethanesulfonyl and X has the same meaning as before. The reaction takes place under the same conditions as the coupling of (4) and (5), although the preferred catalyst is [1,1'-bis(diphenylphosphino)ferrocene]dichloropalladium(II).

Triflates (6) are prepared from phenols (7) by reaction with triflic anhydride:

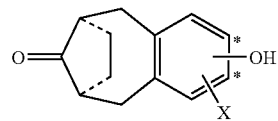
(7)

where and X has the same meaning as before. The reaction takes place in dichloromethane solution at 0° C. in the presence of a base such as pyridine.

The phenols (7) in which X is H are known in the literature (J. Org. Chem. 1982, 47, 4329), and the other compounds of formula (7) may be prepared analogously, or by suitable manipulation (e.g. halogenation) of (7) (X=H).

Pyrazoles (5) in which L is trirlate are accessible from the reaction of alkynes Ar—C≡C—$CO_2Me$ with $R^1NHNH_2$ and treatment of the resulting pyrazolones with triflic anhydride. Pyrazoles (5) in which L is Br are available by reaction of nonaflates (8) with ArZnBr:

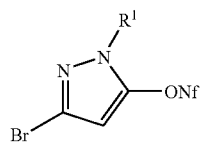

(8)

where Nf represents nonafluorobutanesulfonyl, and Ar and R¹ have the same meaning as before.

Compounds of formula I in which Y represents NR³ may also be prepared by condensation of ketones (3b) with $R^2R^3NSO_2NH_2$, followed by reduction of the resulting sulfamoyl imine. The condensation may be carried out by refluxing the reagents in TBF in the presence of titanium(IV) ethoxide for 16 hours, while the reduction may be carried out using sodium borohydride in methanol at 0° C.

A further route to compounds of formula I in which Y represents O or NR³ comprises reaction of amines (1) with catechol sulfate and treatment of the resulting (2-hydroxyphenyl)sulfamates with $R^2OH$ or $R^2R^3NH$ as appropriate.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free-base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

In a preferred route to enantiomerically pure compounds of formula I, racemic intermediates (7) are subjected to preparative chiral HPLC to provide the corresponding homochiral intermediates, which are then converted to homochiral compounds of formula I by the routes indicated above.

Where they are not commercially available, the starting materials and reagents used in the above-described synthetic schemes may be prepared by conventional means.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

An assay which can be used to determine the level of activity of compounds of the present invention is described in WO01/70677. A preferred assay to determine such activity is as follows:

1) SH-SY5Y cells stably overexpressing the βAPP C-terminal fragment SPA4CT, are cultured at 50–70% confluency. 10 mM sodiumbutyrate is added 4 hours prior to plating.
2) Cells are plated in 96-well plates at 35,000 cells/well/100 μL in Dulbeccos minimal essential medium (DMEM) (phenol red-free)+10% foetal bovine serum (FBS), 50 mM HEPES buffer (pH7.3), 1% glutamine.
3) Make dilutions of the compound plate. Dilute stock solution 18.2× to 5.5% DMSO and 11× final compound concentration. Mix compounds vigorously and store at 4° C. until use.
4) Add 10 μL compound/well, gently mix and leave for 18 h at 37° C., 5% $CO_2$.
5) Prepare reagents necessary to determine amyloid peptide levels, for example by Homogeneous Time Resolved Fluorescence HTRF) assay.
6) Plate 160 μL aliquots of HTRF reagent mixture to each well of a black 96-well HTRF plate.
7) Transfer 40 μL conditioned supernatant from cell plate to HTRF plate. Mix and store at 4° C. for 18 hours.
8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.
9) Add 10 μL/well MTS/PES solution to the cells; mix and leave at 37° C.
10) Read plate when the absorbance values are approximately 0.4–0.8. (Mix briefly before reading to disperse the reduced formazan product).
11) Quantitate amyloid beta 40 peptide using an HTRF plate reader. Alternative assays are described in *Biochemistry*, 2000,39(30), 8698–8704. See also, *J. Neuroscience Methods*, 2000, 102, 61–68.

The compounds of the present invention show unexpectedly high affinities as measured by the above assays. Thus the following Examples all had an $ED_{50}$ of less than 50 nM, typically less than 10 nM, and frequently less than 1 nM in at least one of the above assays. In general, the compounds also exhibit good oral bioavailability and/or brain penetration.

The following examples illustrate the present invention.

EXAMPLES

Intermediate A

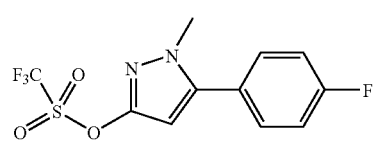

To a solution of methyl 4-(fluorophenyl)propynoate (*J. Org. Chem.* 1987, 52(16), 3662–8) (13 g, 73 mmol) in methanol (60 ml) was added water (60 ml) followed by methylhydrazine (4 ml, 77 mmol), the mixture was stirred for 6 hrs at 60° C. then left to stand overnight. The solid was filtered and washed with water then a minimum volume of methanol and dried overnight, affording 7.7 g of 5-(4-fluorophenyl)-1-methyl-1,2-dihydropyrazol-3-one (55%). δ (¹H, 500 MHz, $CDCl_3$) 3.68 (3H, s), 5.68 (1H, s), 7.13–7.17 (2H, m), 7.37–7.40 (2H, m).

To a cooled suspension of the above pyrazolone (15.5 g, 81 mmol) in dry pyridine (100 ml) was added in three portions trifluoromethanesulfonic anhydride (24 g, 85 mmol) maintaining the temperature below 5° C. The cooling bath was then removed and the reaction was stirred for two hours before pouring into 2M hydrochloric acid and extracting into ethyl acetate. The organic layer was washed with brine, saturated sodium hydrogen carbonate, and dried (sodium sulfate), filtered and evaporated to yield a residue which was dissolved in toluene and evaporated and then dissolved in isohexane and filtered through a plug of silica, eluting with dichloromethane. The solvent was evaporated to yield product as a colourless oil (23.4 g, 89%) δ ($^1$H, 500 MHz, CDCl$_3$) 3.80 (3H, s), 6.14 (1H, s), 7.15–7.19 (2H, m), 7.38–7.42 (2H, m).

Intermediate B

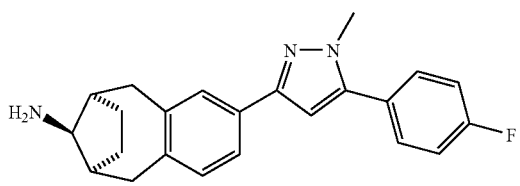

Step 1

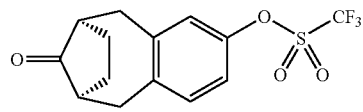

Racemic 2-hydroxy-5,6,7,8,9,10-hexahydro-6,9-methanobenzo[a][8]annulen-11-one (*J. Org. Chem*, 1982, 47, 4329) was resolved using a Berger SFC semi-preparative instrument (chiralpak AS (25×2 cm, 20 um); 15% MeOH/ CO$_2$@ 50 mL/min; 35° C.; 100 bar), retaining the second eluted enantiomer.

To a stirred solution of the homochiral phenol (6.83 g, 34 mmol) in dry DCM (40 mL) at 0° C. under nitrogen was added pyridine (3.8 mL, 47 mmol) followed by triflic anhydride (8.0 mL, 47 mmol). The reaction was stirred at 0° C. for 2 hours, water (40 mL) added, the layers separated, and the aqueous layer extracted with DCM (x2). The combined extracts were washed with brine (x1), dried (MgSO$_4$), filtered and evaporated. The residue was purified by chromatography on silica, eluting with 10–15% EtOAc/hexane, to give the triflate (9.64 g, 85%). (400 MHz $^1$H, δ-CDCl$_3$) 1.28 (2H, m), 1.92 (2H, m), 2.64 (2H, m), 2.85–3.05 (4H, m), 7.13 (2H, m), 7.29 (1H, m).

Step 2

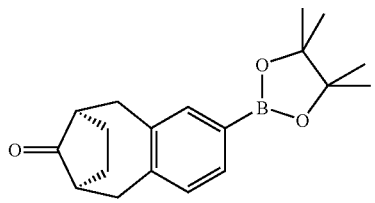

A solution of the triflate from Step 1 (9.64 g, 29 mmol), 1,1'-bis (diphenylphosphino)ferrocene (1.60 g, 2.8 mmol), bis(pinacolato)diboron (8.05 g, 32 mmol) and KOAc (8.49 g, 86 mmol) in dry DMF (200 mL) was deoxygenated by bubbling nitrogen through the solution for 20 minutes. [1,1'-Bis (diphenylphosphino)ferrocene] palladium (II) chloride (2.354 g, 2.9 mmol) was added and deoxygenation was continued for a further 10 minutes. The reaction was heated at 10° C. for 4 hours, then allowed to cool and diluted with water (400 mL). The catalyst was removed by filtration through Hyflo® and the filtrate was extracted with EtOAc (x3). The combined extracts were washed with water then brine, dried (MgSO$_4$), filtered and evaporated. The residue was purified by chromatography on silica, eluting with 10–20% EtOAc/hexane to give the product (7.39 g, 82%). (360 MHz $^1$H, δ-CDCl$_3$) 1.29 (2H, m), 1.35 (12H, s), 1.85 (2H, m), 2.59 (2H, m), 2.84–3.01 (4H, m), 7.21 (1H, m), 7.63 (2H, m).

Step 3

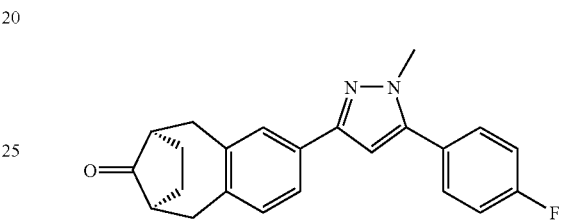

A solution of the boronate from Step 2 (2.06 g, 6.6 mmol), Intermediate A (1.95 g, 6.0 mmol), and sodium carbonate (0.70 g, 6.6 mmol) in dry DMF (30 mL) was deoxygenated by bubbling nitrogen through the solution for 30 minutes. Tetrakis (triphenylphosphine) palladium (0) (0.52 g, 0.45 mmol) was added and deoxygenation was continued for a further 10 minutes. The reaction was heated at 100° C. for 16 hours then allowed to cool and diluted with water (40 mL). The catalyst was removed by filtration through Hyflo® and the filtrate was extracted with EtOAc (x3). The combined extracts were washed with water then brine, dried (MgSO$_4$), filtered and evaporated. The residue was purified by chromatography on silica, eluting with 10-40% EtOAc/ hexane to give the product (1.52 g, 64%). (400 MHz $^1$H, δ-CDCl$_3$) 1.37 (2H, m), 1.87 (2H, m), 2.61 (2H, m), 2.89–3.09 (4H, m), 3.91 (3H, s), 6.58 (1H, s), 7.15–7.26 (3H, m), 7.44 (2H, m), 7.61 (1H, m), 7.71 (1H, m). MS (ES+) 361, MH$^+$.

Step 4

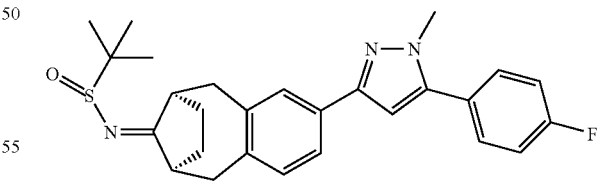

1,1-Dimethylethylsulfinamide (392 mg, 6.0 mmol) followed by titanium tetraethoxide (1.2 ml, 5.6 mmol) were added to a solution of the product from Step 3 (1.0 g, 2.8 mmol) in THF (20 ml), under a nitrogen atmosphere, and the mixture was heated at reflux for 24 hours. The mixture was cooled to room temperature and poured onto rapidly stirring brine. After 30 minutes ethyl acetate (100 ml) was added and the mixture was filtered through a bed of Hyflo®, the phases were separated and the aqueous layer extracted with ethyl acetate (100 ml). The organics were washed with brine, dried (MgSO₄) and evaporated in vacuo to give the desired imine as a yellowish foam (1.3 g, 99%) M/Z ES+ (464) (MH)⁺.

Step 5

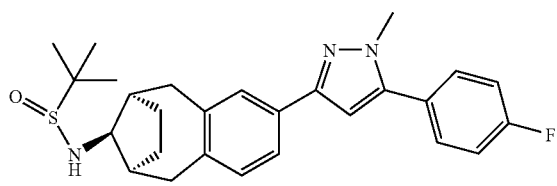

A solution of the imine from Step 4 (1.3 g, 2.8 mmol) in methanol (40 ml) at 0° C., under a nitrogen atmosphere, was treated with sodium borohydride (212 mg, 5.6 mmol) and the mixture was stirred at 0° C. for 45 minutes and at 4° C. for 16 hours. The reaction was concentrated in vacuo, the residue was diluted with water (40 ml) and extracted with ethyl acetate (2×40 ml). The organics were washed with brine, dried (MgSO₄) and evaporated in vacuo to give the desired sulfinamide as a brown foam (1.3 g, 99%) M/Z ES+ (466) (MH)⁺.

Step 6

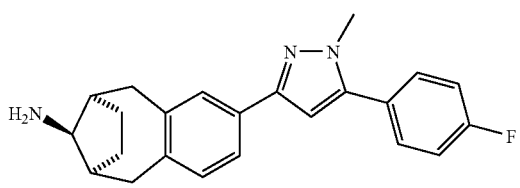

A solution of the sulfinamide from Step 5 (1.3 g, 2.8 mmol) in anhydrous methanol (20 ml) at 0° C. was treated with hydrogen chloride (4N in dioxane, 8 ml, 32 mmol) and the reaction was stirred at 0° C. for one hour. The reaction was evaporated in vacuo, the residue was diluted with sodium bicarbonate (sat, 40 ml) and extracted with ethyl acetate (2×30 ml). The organics were washed with brine, dried (MgSO₄) and evaporated in vacuo to a brown gum which was purified by ion exchange chromatography (SCX, washing with methanol and eluting with ammonia in methanol (2M)) to give the desired amine as a white foam (911 mg, 90%). M/Z ES+ (362) (MH)⁺.

Example 1

N-{(6S,9R,11R)-2-[5-4-fluoroophenyl)-1-methyl-1H-pyrazol-3-yl]-5,6,7,8,9,10-hexahydro-6,9-methanobenzo[a][8]annulen-11-yl}-N'-(2,2,2-trifiuoroethyl)sulfamide

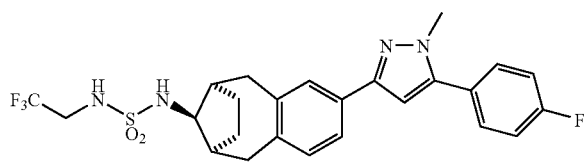

A solution of Intermediate B (50 mg, 0.14 mmol) in dichloromethane (1 ml) was added to trifluoroethylsulfa-moyl chloride (41 mg, 0.2 mmol), triethylamine (78 Tl, 0.56 mmol) was added and the mixture was stirred at room temperature for 16 hours. The reaction was quenched by the addition of water (2 ml) and the phases were separated via a Bond Elute™ phase separation cartridge. The aqueous phase was extracted with dichloromethane and the combined organics were evaporated and purified by Mass Directed LCMS to give the title compound a white foam (42 mg, 58%). M/Z ES+ (523) (MH)⁺.

The following examples were prepared in an analogous fashion, using the appropriate sulfamoyl chloride:

| Example | R | m/z (MH)⁺ |
|---|---|---|
| 2 | F₃C—⟨piperidinyl⟩-N- | 577 |
| 3 | propyl-NH- | 483 |
| 4 | propyl-N(CH₃)- | 497 |
| 5 | cyclobutyl-CH₂-NH- | 495 |

Example 6

N-{(6S,9R,11R)-2-[5-(4-fluorophenyl)-1-methyl-1H-pyrazol-3-yl]-5,6,7,8,9,10-hexahydro-6,9-methanobenzo[a][8]annulen-11-yl}pyrrolidine-1-sulfonamide

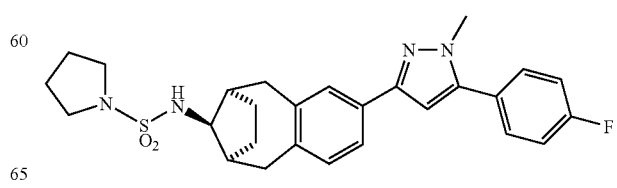

Step 1

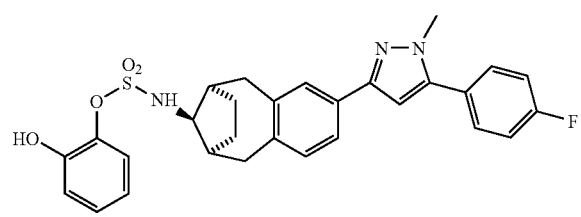

A solution of Intermediate B (400 mg, 1.1 mmol) in THF (8 ml), under a nitrogen atmosphere, was treated with catchol sulfate (200 mg, 1.2 mmol) and the mixture was stirred at room temperature for 65 hours. More catchol sulfate (200 mg, 1.2 mmol) was added and the mixture was stirred at room temperature for 20 hours. The reaction was diluted with ammonium chloride solution (sat, 40 ml) and extracted with ethyl acetate (2×20 ml). The organics were washed with brine, dried (MgSO$_4$) and evaporated in vacuo to give a purple gum, which was purified by chromatography on silica [ethyl acetate:isohexane 1:2] to give the desired sulfamate as a white foam (368 mg, 68%) M/Z ES+ (534) (MH)$^+$.

Step 2

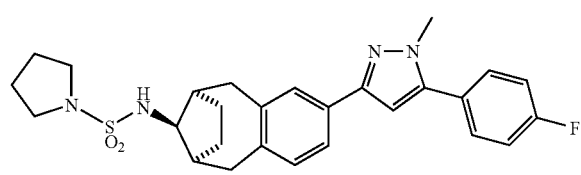

A solution of the sulfamate from step 1 (50 mg, 0.09 mmol), and pyrrolidine (40 Tl, 0.46 mmol) in dioxane (1 ml), under a nitrogen atmosphere was heated at 80° C. for 1 hour. The reaction was diluted with water and extracted with DCM (3×20 ml). The extracts were dried (MgSO$_4$) and evaporated in vacuo to a brown gum which was purified by chromatography on silica [ethyl acetate:isohexane 1:2] to give the desired sulfamide as a white foam (40 mg, 91%) MIZ ES+(495) (MH)$^+$.

Example 7

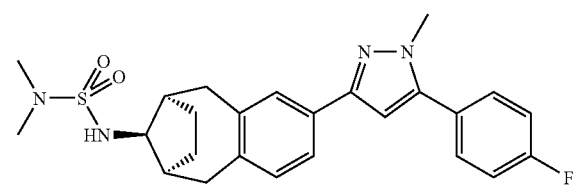

Step 1

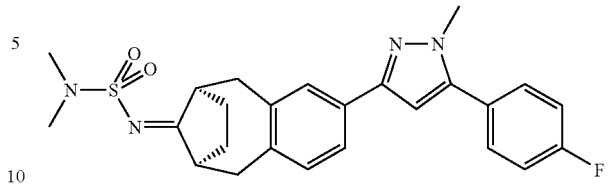

A solution of the ketone from Step 3 of the preparation of Intermediate B (0.360 g, 1.0 mmol), N,N-dimethylsulfamide (0.620 g, 5.0 mmol) and titanium(IV) ethoxide (tech., 0.63 mL, 3.0 mmol) in dry THF (5 mL) was stirred and heated at reflux under nitrogen for 16 hours. The reaction was allowed to cool to room temperature and poured into rapidly stirred brine (60 mL). The mixture was stirred for 1 hour, then filtered through Hyflo□, washing with EtOAc. The layers of the filtrate were separated, and the aqueous layer was extracted with EtOAc. The combined organic extracts were washed with brine, dried (MgSO$_4$), filtered and evaporated. The residue was purified by chromatography on silica, eluting with 5–20% EtOAc/DCM, to give the imine (0.383 g, 82%). MS (ES+) 467, MH$^+$.

Step 2

A solution of the imine from Step 1 (60 mg, 0.13 mmol) and sodium borohydride (10 mg, 0.26 mmol) in MeOH (5 mL) was stirred at 0° C. for 1 hour. The reaction was concentrated in vacuo and water (10 mL) was added, then the mixture was extracted with EtOAc, and the combined organic extracts were washed with brine, dried (MgSO$_4$), filtered and evaporated. The residue was purified by chromatography on silica, eluting with 30% EtOAc/hexane, to give the sulfamide (43 mg, 73%). (360 MHz $^1$H, δ-CDCl$_3$) 1.25 (2H, m), 1.70 (2H, m), 2.50 (2H, m), 2.71 (2H, m), 2.87 (6H, s), 3.10 (2H, m), 3.80 (1H, m), 3.90 (3H, s), 4.59 (1H, m), 6.56 (1H, s), 7.15 (3H, m), 7.43 (2H, m), 7.51 (1H, m), 7.60 (1H, m). MS (ES+) 469, MH$^+$.

Example 8

N-{(6S,9R,11R)-2-[5-(4-fluorophenyl)-1-methyl-1H-pyrazol-3-yl]-5,6,7,8,9,10-hexahydro-6,9-methanobenzo[a][8]annulen-11-yl}butane-1-sulfonamide

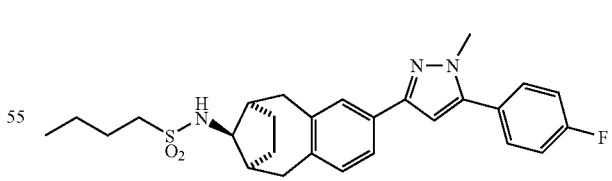

A solution of Intermediate B (50 mg, 0.14 mmol) in dichloromethane (1 ml) was added to n-butanesulfonyl chloride (44 mg, 0.28 mmol), followed by triethylamine (78 Tl, 0.56 mmol), and the mixture was stirred at room temperature for 16 hours. The reaction was quenched by the addition of water (2 ml) and the phases were separated via Bond Elute™ phase separation cartridge. The aqueous phase was extracted with dichloromethane, the combined organics were evaporated and the residue purified by Mass Directed LCMS to give the title compound a white foam M/Z ES+ (482) (MH)+.

The following examples were prepared in an analogous fashion using the appropriate sulfonyl chloride:

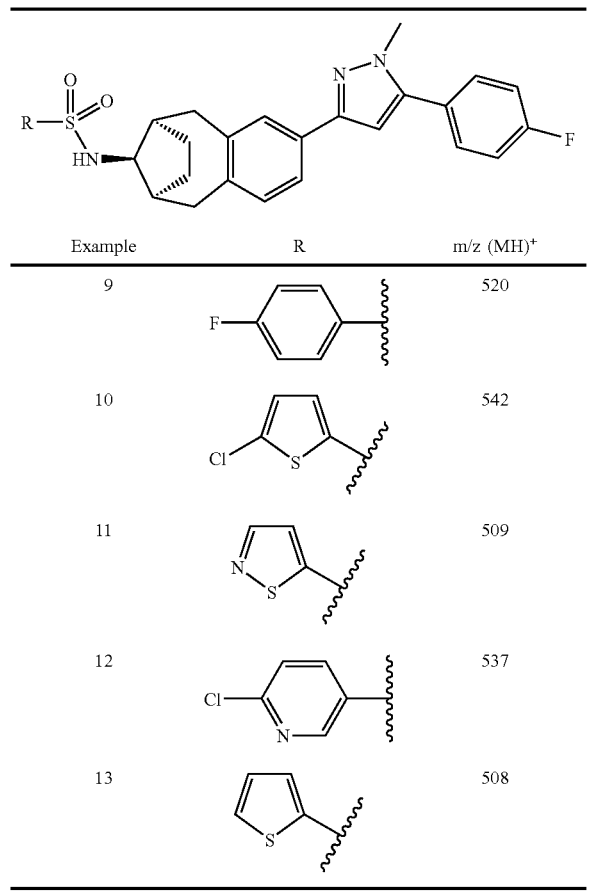

| Example | R | m/z (MH)+ |
|---|---|---|
| 9 |  | 520 |
| 10 |  | 542 |
| 11 |  | 509 |
| 12 |  | 537 |
| 13 |  | 508 |

Example 14

Propyl (6S,9R,11R)-2-[5-(4-fluorophenyl)-1-methyl-1H-pyrazol-3-yl]-5,6,7,8,9,10-hexahydro-6,9-methanobenzo[a][8]annulen-11-ylsulfamate

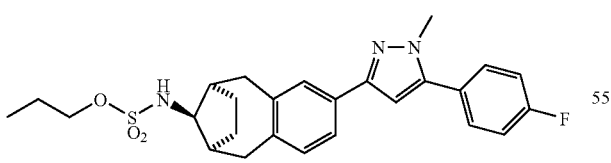

A solution of the sulfamate from Example 6 step 1 (43 mg, 0.08 mmol) and triethylamine (14 Tl, 0.1 mmol) in n-propanol (1 ml), under a nitrogen atmosphere, was heated at 80° C. for 16 hours. The reaction was cooled to room temperature, diluted with ethyl acetate and washed with sodium hydroxide solution (1N, 3×10 ml), followed by water (10 ml) and brine. The organics were dried (MgSO4) and evaporated in vacuo to a brown gum, which was purified by chromatography on silica [ethyl acetate:isohexane 1:2] to give the desired sulfamate as a white foam (36 mg, 93%) M/Z ES+ (484) (MH)+.

Example 15

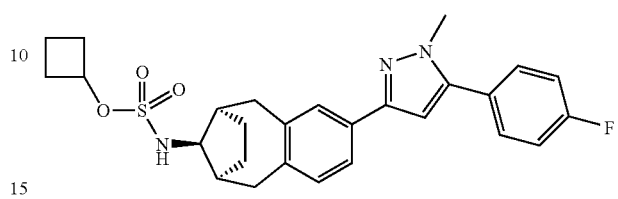

Prepared by the method of Example 14, substituting cyclobutanol for n-propanol. M/Z ES+ (496) (MH)+.

Examples 16

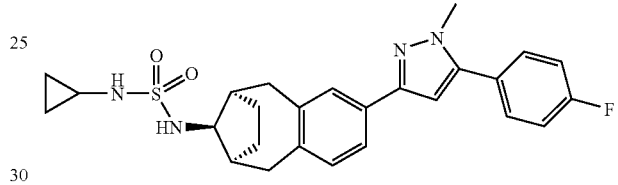

Prepared by the method of Example 6, substituting cyclopropylamine for pyrrolidine. M/Z ES+ (481) (MH)+.

The invention claimed is:

1. A compound of formula I:

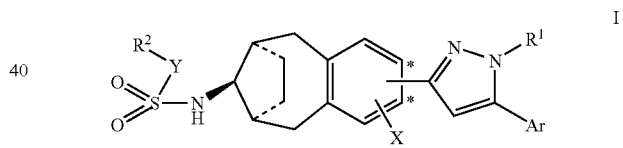

wherein the pyrazole group is attached at one of the positions indicated by an asterisk and X is attached at a position adjacent thereto;

X represents H, OH, $C_{1-4}$alkoxy, Cl or F;

Y represents a bond, O or $NR^3$;

Ar represents phenyl or 6-membered heteroaryl, either of which bears 0–3 substituents independently selected from halogen, $CF_3$, $CHF_2$, $CH_2F$, $NO_2$, CN, $OCF_3$, $C_{1-6}$alkyl and $C_{1-6}$alkoxy;

$R^1$ represents a hydrocarbon group of 1–5 carbon atoms which is optionally substituted with up to 3 halogen atoms; and $R^2$ represents a hydrocarbon group of 1–10 carbon atoms which is optionally substituted with up to 3 halogen atoms, or heteroaryl of 5 or 6 ring atoms optionally bearing up to 3 substituents independently selected from halogen, $CF_3$, $CHF_2$, $CH_2F$, $NO_2$, CN, $OCF_3$, $C_{1-6}$alkyl and $C_{1-6}$alkoxy; or when Y represents $NR^3$, $R^2$ and $R^3$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy;

R³ represents H or $C_{1-4}$alkyl, or together with R² completes a heterocyclic ring as defined above;
or a pharmaceutically acceptable salt thereof.

2. A compound according to claim 1 of formula IIa:

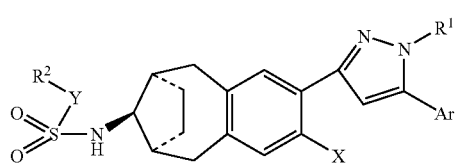

or formula IIIa:

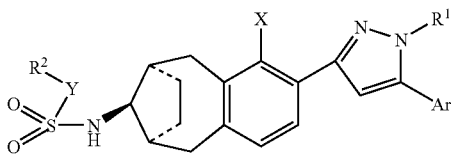

wherein X, Y, Ar, R¹ and R² are as defined in claim 1;
or a pharmaceutically acceptable salt thereof.

3. A compound according to claim 1 wherein X represents H.

4. A compound according to claim 1 wherein Y is a bond and R² represents optionally substituted phenyl or heteroaryl or $C_{1-6}$alkyl.

5. A compound according to claim 1 wherein Y is O and R² represents alkyl or cycloalkyl of up to 6 carbon atoms.

6. A compound according to claim 1 wherein Y is NH or NMe and R² represents alkyl or cycloalkyl of up to 6 carbon atoms which is optionally substituted with up to 3 fluorine atoms.

7. A compound according to claim 1 wherein Y is NR³ and R² and R³ complete a heterocyclic ring.

8. A pharmaceutical composition comprising a compound according to claim 1 and a pharmaceutically acceptable carrier.

9. A method of treatment of a subject suffering from Alzheimer's disease which comprises administering to that subject an effective amount of a compound according to claim 1.

10. A method of preparing a compound according to claim 1 comprising reaction of an amine (1) with R²—Y—SO₂Cl:

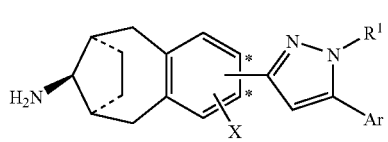

where X, Y, Ar, R¹ and R² and are as defined in claim 1.

* * * * *